US009796983B2

(12) United States Patent
Narva et al.

(10) Patent No.: US 9,796,983 B2
(45) Date of Patent: Oct. 24, 2017

(54) **COMBINATIONS INCLUDING CRY3AA AND CRY6AA PROTEINS TO PREVENT DEVELOPMENT OF RESISTANCE IN CORN ROOTWORMS (*DIABROTICA* SPP.)**

(75) Inventors: Kenneth E. Narva, Zionsville, IN (US); Thomas Meade, Zionsville, IN (US); Kristin J. Fencil, San Diego, CA (US); Huarong Li, Zionsville, IN (US); Timothy D. Hey, Zionsville, IN (US); Aaron T. Woosley, Fishers, IN (US); Monica B. Olson, Lebanon, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 493 days.

(21) Appl. No.: 13/643,052

(22) PCT Filed: Apr. 22, 2011

(86) PCT No.: PCT/US2011/033622
§ 371 (c)(1),
(2), (4) Date: Jun. 10, 2013

(87) PCT Pub. No.: WO2011/133896
PCT Pub. Date: Oct. 27, 2011

(65) Prior Publication Data
US 2013/0263331 A1    Oct. 3, 2013

Related U.S. Application Data

(60) Provisional application No. 61/327,240, filed on Apr. 23, 2010, provisional application No. 61/388,273, (Continued)

(51) Int. Cl.
*A01H 5/10* (2006.01)
*A01N 25/00* (2006.01)
(Continued)

(52) U.S. Cl.
CPC ......... *C12N 15/8286* (2013.01); *A01G 1/001* (2013.01); *A01H 5/10* (2013.01);
(Continued)

(58) Field of Classification Search
None
See application file for complete search history.

(56) References Cited

U.S. PATENT DOCUMENTS

| 1,558,396 | A | * | 10/1925 | Roehrs | A01C 7/02 222/564 |
| 5,874,288 | A | * | 2/1999 | Thompson | C07K 14/325 424/93.2 |

(Continued)

FOREIGN PATENT DOCUMENTS

WO    WO 2008121633 A1  * 10/2008

OTHER PUBLICATIONS

Tang et al, Mol Breeding (2006) vol. 18 pp. 1-10).*
(Continued)

*Primary Examiner* — Lee A Visone
*Assistant Examiner* — Weihua Fan
(74) *Attorney, Agent, or Firm* — Ronald S. Maciak; Barnes & Thornburg LLP (57) ABSTRACT

The subject invention relates in part to Cry3Aa in combination with Cry6Aa. The subject invention relates in part to the surprising discovery that combinations of Cry3Aa and Cry6Aa are useful for preventing development of resistance (to either insecticidal protein system alone) by a corn rootworm (*Diabrotica* spp.) population. Included within the subject invention are plants producing these insecticidal Cry proteins, which are useful to mitigate concern that a corn rootworm population could develop that would be resistant to either of these insecticidal protein systems alone. The subject invention also relates in part to combinations of
(Continued)

Binding of $^{125}$I-Cry3Aa trypsin core (A) and $^{125}$I-Cry6Aa (full-length) (B) as a function of input radiolabeled Cry toxins to BBMV prepared from western corn rootworm larvae. Specific binding =total binding − non-specific binding, error bar=SEM (standard error of mean).

Cry3Aa and Cry6Aa proteins "triple-stacked" or "multi-stacked" with another insecticidal protein(s) such as a Cry6Aa protein or binary Cry34/35 proteins. Thus, such embodiments target rootworms with three modes of action. Transgenic plants, including corn, comprising a cry6Aa gene and a cry3Aa gene are included within the scope of the subject invention.

21 Claims, 2 Drawing Sheets

Related U.S. Application Data filed on Sep. 30, 2010, provisional application No. 61/476,005, filed on Apr. 15, 2011, provisional application No. 61/477,447, filed on Apr. 20, 2011.

(51) Int. Cl.

| | |
|---|---|
| *C12N 15/82* | (2006.01) |
| *C07K 14/195* | (2006.01) |
| *C07K 14/325* | (2006.01) |
| *A01N 37/18* | (2006.01) |
| *B65D 85/00* | (2006.01) |
| *A01G 1/00* | (2006.01) |
| *A01N 43/50* | (2006.01) |
| *B32B 1/02* | (2006.01) |

(52) U.S. Cl.

CPC ............. *A01N 37/18* (2013.01); *A01N 43/50* (2013.01); *B32B 1/02* (2013.01); *B65D 85/00* (2013.01); *C07K 14/325* (2013.01); *Y10T 428/13* (2015.01)

(56) References Cited

U.S. PATENT DOCUMENTS

| | | | | |
|---|---|---|---|---|
| 6,551,962 B1 | 4/2003 | Pershing et al. | | |
| 6,620,988 B1 | 9/2003 | English et al. | | |
| 2001/0010932 A1* | 8/2001 | Schnepf | A01N 37/46 | 435/252.33 |
| 2002/0106768 A1* | 8/2002 | Thompson | C07K 14/325 | 435/184 |
| 2003/0120054 A1* | 6/2003 | Chen | C12N 15/8286 | 536/23.2 |
| 2007/0011773 A1* | 1/2007 | Clough | A01N 63/02 | 800/279 |
| 2009/0019609 A1* | 1/2009 | Romano | C12N 15/8286 | 800/302 |
| 2010/0017914 A1* | 1/2010 | Hart | C07K 14/325 | 800/279 |

OTHER PUBLICATIONS

Bates et al, Nature Biotechnology (2005) vol. 23 pp. 57-62.*
Tang et al (Mol Breeding (2006) vol. 18 pp. 1-10).*
Crickmore et al, Microbiology and Molecular Biology Reviews, Sep. 1998, pp. 807-813.*
De Maagd et al, Trends in Genetics (2001) 17: 193-199.*
Escriche, Baltasar, et al. "Immunohistochemical detection of binding of CrylA crystal proteins of Bacillus thuringiensis in highly resistant strains of *Plutella xylostella* (L.) from Hawaii." Biochemical and biophysical research communications 212.2 (1995): 388-395.*
Friedberg, Iddo. "Automated protein function prediction—the genomic challenge." Briefings in bioinformatics 7.3 (2006): 225-242.*
Kaiser-Alexnat et al.: "Protease activities in the midgut of Western corn rootworm (Diabrotica virgifera virgifera LeConte)", Journal of Invertebrate Pathology, San Diego, CA, US, vol. 100, No. 3, Mar. 2, 2009 (Mar. 2, 2009).
International Search Report dated Jul. 8, 2011 of International Application No. PCT/US2011/033622.
Bravo et al., "How to cope wtih insect resistance to Bt toxins?", Trends in Biotechnology vol. 26, No. 10.

* cited by examiner

Figure 1. Binding of $^{125}$I-Cry3Aa trypsin core (A) and $^{125}$I-Cry6Aa (full-length) (B) as a function of input radiolabeled Cry toxins to BBMV prepared from western corn rootworm larvae. Specific binding =total binding − non-specific binding, error bar=SEM (standard error of mean).

Figure 2. Binding of $^{125}$I-Cry3Aa to BBMV prepared from western corn rootworm larvae at different concentrations of non-labeled competitor (log 0.1=-1.0, log 1=0, log10=1.0, log100=2.0, log1000=3.0).

COMBINATIONS INCLUDING CRY3AA AND CRY6AA PROTEINS TO PREVENT DEVELOPMENT OF RESISTANCE IN CORN ROOTWORMS (*DIABROTICA* SPP.)

CROSS-REFERENCE TO RELATED APPLICATIONS

This is a national phase application, filed pursuant to 35 U.S.C. §371, of PCT application No. PCT/US2011/033622 filed on Apr. 22, 2011, which claims the benefit of U.S. provisional application No. 61/327,240, filed on Apr. 23, 2010, U.S. provisional application No. 61/388,273, filed on Sep. 30, 2010, U.S. provisional application No. 61/476,005, filed on Apr. 15, 2011, and U.S. provisional application No. 61/477,447, filed on Apr. 20, 2011. The prior applications are incorporated herein by reference in their entirety.

BACKGROUND

Humans grow corn for food and energy applications. Corn is an important crop. It is an important source of food, food products, and animal feed in many areas of the world. Insects eat and damage plants and thereby undermine these human efforts. Billions of dollars are spent each year to control insect pests and additional billions are lost to the damage they inflict.

Damage caused by insect pests is a major factor in the loss of the world's corn crops, despite the use of protective measures such as chemical pesticides. In view of this, insect resistance has been genetically engineered into crops such as corn in order to control insect damage and to reduce the need for traditional chemical pesticides.

Over 10 million acres of U.S. corn are infested with corn rootworm species complex each year. The corn rootworm species complex includes the northern corn rootworm (*Diabrotica barberi*), the southern corn rootworm (*D. undecimpunctata howardi*), and the western corn rootworm (*D. virgifera virgifera*). (Other species include *Diabrotica virgifera zeae* (Mexican corn rootworm), *Diabrotica balteata* (Brazilian corn rootworm), and Brazilian corn rootworm complex (*Diabrotica viridula* and *Diabrotica speciosa*).)

The soil-dwelling larvae of these *Diabrotica* species feed on the root of the corn plant, causing lodging. Lodging eventually reduces corn yield and often results in death of the plant. By feeding on cornsilks, the adult beetles reduce pollination and, therefore, detrimentally affect the yield of corn per plant. In addition, adults and larvae of the genus *Diabrotica* attack cucurbit crops (cucumbers, melons, squash, etc.) and many vegetable and field crops in commercial production as well as those being grown in home gardens.

Synthetic organic chemical insecticides have been the primary tools used to control insect pests but biological insecticides, such as the insecticidal proteins derived from *Bacillus thuringiensis* (Bt), have played an important role in some areas. The ability to produce insect-resistant plants through transformation with Bt insecticidal protein genes has revolutionized modern agriculture and heightened the importance and value of insecticidal proteins and their genes.

Insecticidal crystal proteins from some strains of *Bacillus thuringiensis* (B.t.) are well-known in the art. See, e.g., Hofte et al., Microbial Reviews, Vol. 53, No. 2, pp. 242-255 (1989). These proteins are typically produced by the bacteria as approximately 130 kDa protoxins that are then cleaved by proteases in the insect midgut, after ingestion by the insect, to yield a roughly 60 kDa core toxin. These proteins are known as crystal proteins because distinct crystalline inclusions can be observed with spores in some strains of B.t. These crystalline inclusions are often composed of several distinct proteins.

One group of genes which have been utilized for the production of transgenic insect resistant crops are the delta-endotoxins from *Bacillus thuringiensis* (B.t.). Delta-endotoxins have been successfully expressed in crop plants such as cotton, potatoes, rice, sunflower, as well as corn, and have proven to provide excellent control over insect pests. (Perlak, F. J et al. (1990) Bio/Technology 8, 939-943; Perlak, F. J. et al. (1993) Plant Mol. Biol. 22: 313-321; Fujimoto H. et al. (1993) Bio/Technology 11: 1151-1155; Tu et al. (2000) Nature Biotechnology 18:1101-1104; PCT publication number WO 01/13731; and Bing J W et al. (2000) Efficacy of Cry1F Transgenic Maize, $14^{th}$ Biennial International Plant Resistance to Insects Workshop, Fort Collins, Colo.)

Several Bt proteins have been used to create the insect-resistant transgenic plants that have been successfully registered and commercialized to date. These include Cry1Ab, Cry1Ac, Cry1F, Cry1A.105, Cry2Ab, Cry3Aa, Cry3Bb, and Cry34/35Ab in corn, Cry1Ac and Cry2Ab in cotton, and Cry3A in potato.

The commercial products expressing these proteins express a single protein except in cases where the combined insecticidal spectrum of 2 proteins is desired (e.g., Cry1Ab and Cry3Bb in corn combined to provide resistance to lepidopteran pests and rootworm, respectively) or where the independent action of the proteins makes them useful as a tool for delaying the development of resistance in susceptible insect populations (e.g., Cry1Ac and Cry2Ab in cotton combined to provide resistance management for tobacco budworm).

Some of the qualities of insect-resistant transgenic plants that have led to rapid and widespread adoption of this technology also give rise to the concern that pest populations will develop resistance to the insecticidal proteins produced by these plants. Several strategies have been suggested for preserving the utility of Bt-based insect resistance traits which include deploying proteins at a high dose in combination with a refuge, and alternation with, or co-deployment of, different toxins (McGaughey et al. (1998), "B.t. Resistance Management," *Nature Biotechnol.* 16:144-146).

The proteins selected for use in an Insect Resistance Management (IRM) stack should be active such that resistance developed to one protein does not confer resistance to the second protein (i.e., there is not cross resistance to the proteins). If, for example, a pest population selected for resistance to "Protein A" is sensitive to "Protein B", one would conclude that there is not cross resistance and that a combination of Protein A and Protein B would be effective in delaying resistance to Protein A alone.

In the absence of resistant insect populations, assessments can be made based on other characteristics presumed to be related to cross-resistance potential. The utility of receptor-mediated binding in identifying insecticidal proteins likely to not exhibit cross resistance has been suggested (van Mellaert et al. 1999). The key predictor of lack of cross resistance inherent in this approach is that the insecticidal proteins do not compete for receptors in a sensitive insect species.

In the event that two Bt toxins compete for the same receptor, then if that receptor mutates in that insect so that one of the toxins no longer binds to that receptor and thus is no longer insecticidal against the insect, it might be the case that the insect will also be resistant to the second toxin (which competitively bound to the same receptor). That is, the insect is said to be cross-resistant to both Bt toxins. However, if two toxins bind to two different receptors, this could be an indication that the insect would not be simultaneously resistant to those two toxins.

A relatively newer insecticidal protein system was discovered in *Bacillus thuringiensis* as disclosed in WO 97/40162. This system comprises two proteins—one of approximately 14-15 kDa and the other of about 44-45 kDa. See also U.S. Pat. Nos. 6,083,499 and 6,127,180. These proteins have now been assigned to their own classes, and accordingly received the Cry designations of Cry34 and Cry35, respectively. See Crickmore et al. website (biols.susx.ac.uk/home/Neil_Crickmore/Bt/). Many other related proteins of this type of system have now been disclosed. See e.g. U.S. Pat. No. 6,372,480; WO 01/14417; and WO 00/66742. Plant-optimized genes that encode such proteins, wherein the genes are engineered to use codons for optimized expression in plants, have also been disclosed. See e.g. U.S. Pat. No. 6,218,188.

The exact mode of action of the Cry34/35 system has yet to be determined, but it appears to form pores in membranes of insect gut cells. See Moellenbeck et al., *Nature Biotechnology*, vol. 19, p. 668 (July 2001); Masson et al., *Biochemistry*, 43 (12349-12357) (2004). The exact mechanism of action remains unclear despite 3D atomic coordinates and crystal structures being known for a Cry34 and a Cry35 protein. See U.S. Pat. Nos. 7,524,810 and 7,309,785. For example, it is unclear if one or both of these proteins bind a typical type of receptor, such as an alkaline phosphatase or an aminopeptidase.

Furthermore, because there are different mechanisms by which an insect can develop resistance to a Cry protein (such as by altered glycosylation of the receptor [see Jurat-Fuentes et al. (2002) 68 *AEM* 5711-5717], by removal of the receptor protein [see Lee et al. (1995) 61 *AEM* 3836-3842], by mutating the receptor, or by other mechanisms [see Heckel et al., *J. Inv. Pathol.* 95 (2007) 192-197]), it was impossible to a priori predict whether there would be cross-resistance between Cry34/35 and other Cry proteins. Lefko et al. discusses a complex resistance phenomenon in rootworm. *J. Appl. Entomol.* 132 (2008) 189-204.

Predicting competitive binding for the Cry34/35 system is also further complicated by the fact that two proteins are involved in the Cry34/35 binary system. Again, it is unclear if and how these proteins effectively bind the insect gut/gut cells, and if and how they interact with or bind with each other.

Other options for controlling coleopterans include Cry3Bb toxins, Cry3C, Cry6B, ET29, ET33 with ET34, TIC407, TIC435, TIC417, TIC901, TIC1201, ET29 with TIC810, ET70, ET76 with ET80, TIC851, and others. RNAi approaches have also been proposed. See e.g. Baum et al., *Nature Biotechnology*, vol. 25, no. 11 (November 2007) pp. 1322-1326.

Meihls et al. suggest the use of refuges for resistance management in corn rootworm. PNAS (2008) vol. 105, no. 49, 19177-19182.

BRIEF SUMMARY

The subject invention relates in part to Cry3Aa in combination with Cry6Aa. The subject invention relates in part to the surprising discovery that Cry3Aa and Cry6Aa are useful for preventing development of resistance (to either insecticidal protein system alone) by a corn rootworm (*Diabrotica* spp.) population. As one skilled in the art will recognize with the benefit of this disclosure, plants producing these insecticidal Cry proteins will be useful to mitigate concern that a corn rootworm population could develop that would be resistant to either of these insecticidal protein systems alone.

The subject invention is supported in part by the discovery that components of these Cry protein systems do not compete with each other for binding corn rootworm gut receptors.

The subject invention also relates in part to triple stacks or "pyramids" of three (or more) toxin systems, with Cry3Aa and Cry6Aa being the base pair. Thus, plants (and acreage planted with such plants) that produce these two insecticidal protein systems are included within the scope of the subject invention.

BRIEF DESCRIPTION OF THE SEQUENCES

SEQ ID NO:1: Full-length Cry3Aa protein sequence
SEQ ID NO:2: Cry3Aa trypsin core protein sequence
SEQ ID NO:3: Full-length Cry6Aa1 protein sequence

DETAILED DESCRIPTION

Sequences for Cry3Aa and Cry6Aa proteins are obtainable from *Bacillus thruingiensis* isolates as listed on the Crickmore et al. website (lifesci.sussex.ac.uk/home/Neil_Crickmore/Bt/intro.html).

The subject invention includes the use of Cry3Aa insecticidal proteins in combination with a Cry6Aa toxin to protect corn from damage and yield loss caused by corn rootworm feeding by corn rootworm populations that might develop resistance to either of these Cry protein systems alone (without the other).

The subject invention thus teaches an Insect Resistance Management (IRM) stack to prevent the development of resistance by corn rootworm to Cry6Aa and/or Cry3Aa.

The present invention provides compositions for controlling rootworm pests comprising cells that produce a Cry6Aa insecticidal protein and a Cry3Aa insecticidal protein.

The invention further comprises a host transformed to produce both a Cry6Aa protein and a Cry3Aa insecticidal protein, wherein said host is a microorganism or a plant cell.

It is additionally intended that the invention provides a method of controlling rootworm pests comprising contacting said pests or the environment of said pests with an effective amount of a composition that contains a Cry6Aa protein and further contains a Cry3Aa insecticidal protein.

An embodiment of the invention comprises a maize plant comprising a plant-expressible gene encoding a Cry3Aa insecticidal protein and a plant-expressible gene encoding a Cry6Aa protein, and seed of such a plant.

A further embodiment of the invention comprises a maize plant wherein a plant-expressible gene encoding a Cry3Aa insecticidal protein and a plant-expressible gene encoding a Cry6Aa protein have been introgressed into said maize plant, and seed of such a plant.

As described in the Examples, competitive receptor binding studies using radiolabeled Cry3Aa core toxin protein show that the Cry6Aa core toxin protein does not compete for binding in CRW insect tissue samples to which Cry3Aa binds. See FIG. 2. These results indicate that the combination of Cry6Aa and Cry3Aa proteins is an effective means to mitigate the development of resistance in CRW populations to either protein system alone.

Thus, based in part on the data described above and elsewhere herein, Cry3Aa and Cry6Aa proteins can be used to produce IRM combinations for prevention or mitigation of resistance development by CRW. Other proteins can be added to this combination to expand insect-control spectrum, for example. The subject combination can also be used in some preferred "triple stacks" or "pyramid" in combination with yet another protein for controlling rootworms, such as Cry3Ba or binary Cry34/35 proteins. Such additional combinations would thus provide multiple modes of action against a rootworm. RNAi against rootworms is a still further option. See e.g. Baum et al., Nature Biotechnology, vol. 25, no. 11 (November 2007) pp. 1322-1326.

In light of the disclosure of U.S. Ser. No. 61/327,240 (filed Apr. 23, 2010) relating to combinations of Cry34Ab/35Ab and Cry3Aa proteins, U.S. Ser. No. 61/388,273 (filed Sep. 30, 2010) relating to combinations of Cry34Ab/35Ab and Cry6Aa proteins, and U.S. Ser. No. 61/476,005 (filed Apr. 15, 2011) relating to combinations of Cry34Ab/35Ab and Cry3Ba proteins, some preferred "triple stacks" or "multiple modes of action stacks" of the subject invention include a Cry6Aa protein combined with a Cry3Aa protein, together with and a Cry3Ba protein or binary Cry34/35 proteins. Transgenic plants, including corn, comprising a cry6Aa gene and a cry3Aa gene (optionally with a third or fourth toxin system, e.g., Cry3B and/or Cry34/35) are included within the scope of the subject invention. Thus, such embodiments target the insect with at least three modes of action.

Deployment options of the subject invention include the use of Cry6Aa and Cry3Aa proteins in corn-growing regions where *Diabrotica* spp. are problematic. Another deployment option would be to use one or both of the Cry6Aa and Cry3Aa proteins in combination with other traits.

A person skilled in this art will appreciate that Bt toxins, even within a certain class such as Cry6Aa and Cry3Aa can vary to some extent.

Genes and Toxins.

The term "isolated" refers to a polynucleotide in a non-naturally occurring construct, or to a protein in a purified or otherwise non-naturally occurring state. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins. The same applies to Cry3B's and Cry34/35 if used in triple/multiple stacks according to the subject invention. Domains/subdomains of these proteins can be swapped to make chimeric proteins, for example. See e.g. U.S. Pat. Nos. 7,309,785 and 7,524,810 regarding Cry34/35 proteins. The '785 patent also teaches truncated Cry35 proteins. Truncated toxins are also exemplified herein.

As used herein, the boundaries represent approximately 95% (Cry6Aa's and Cry3Aa's), 78% (Cry6A's and Cry 3A's), and 45% (Cry6's and Cry 3's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. The same applies to Cry3B's and Cry34/35 (e.g. Cry34Ab/Cry35Ab) if used in triple/multiple stacks, for example, according to the subject invention.

It should be apparent to a person skilled in this art that genes encoding active toxins can be identified and obtained through several means. The specific genes or gene portions exemplified herein may be obtained from the isolates deposited at a culture depository. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Genes that encode active fragments may also be obtained using a variety of restriction enzymes. Proteases may be used to directly obtain active fragments of these protein toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments of genes encoding proteins that retain pesticidal activity are also included in this definition.

A further method for identifying the genes encoding the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169-170. Some examples of salt concentrations and temperature combinations are as follows (in order of increasing stringency): 2×SSPE or SSC at room temperature; 1×SSPE or SSC at 42° C.; 0.1×SSPE or SSC at 42° C.; 0.1×SSPE or SSC at 65° C. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Variant Toxins.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be greater than 75%, or preferably greater than 85%, preferably greater than 90%, preferably greater than 95%, preferably greater than 96%, preferably greater than 97%, preferably greater than 98%, or preferably greater than 99% in some embodiments. The amino acid identity will typically be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant Hosts.

The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a Bt strain that expresses both toxins of the subject invention. Other host organisms may also be transformed with one or both of the toxin genes then used to accomplish the synergistic effect. With suitable microbial hosts, e.g., *Pseudomonas*, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest. Non-regenerable/non-totipotent plant cells from a plant of the subject invention (comprising at least one of the subject IRM genes) are included within the subject invention.

Plant Transformation.

A preferred embodiment of the subject invention is the transformation of plants with genes encoding the subject insecticidal protein or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include, but are not limited to, maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. No. 4,945,050 and U.S. Pat. No. 5,141,131). Plants may be transformed using *Agrobacterium* technology, see U.S. Pat. No. 5,177,010, U.S. Pat. No. 5,104,310, European Patent Application No. 0131624B1, European Patent Application No. 120516, European Patent Application No. 159418B1, European Patent Application No. 176112, U.S. Pat. No. 5,149,645, U.S. Pat. No. 5,469,976, U.S. Pat. No. 5,464,763, U.S. Pat. No. 4,940,838, U.S. Pat. No. 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. No. 5,231,019, U.S. Pat. No. 5,463,174, U.S. Pat. No. 4,762,785, U.S. Pat. No. 5,004,863, and U.S. Pat. No. 5,159,135. Other transformation technology includes WHISKERS™ technology, see U.S. Pat. No. 5,302,523 and U.S. Pat. No. 5,464,765. Electroporation technology has also been used to transform plants, see WO 87/06614, U.S. Pat. No. 5,472,869, U.S. Pat. No. 5,384,253, WO 9209696, and WO 9321335. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue types I and II, hypocotyl, meristem, and the like. Almost all plant tissues may be transformed during dedifferentiation using appropriate techniques within the skill of an artisan.

Genes encoding any of the subject toxins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13 mp series, pACYC184, etc. Accordingly, the sequence encoding the Cry protein or variants can be inserted into the vector at a suitable restriction site. The resulting plasmid is used for transformation of cells of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in EP 120516; Lee and Gelvin (2008), Fraley et al. (1986), and An et al. (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as bialaphos, kanamycin, G418, bleomycin, or hygromycin, inter alia. The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic B.t. genes for use in plants are known in the art (Stewart, 2007).

Regardless of transformation technique, the gene is preferably incorporated into a gene transfer vector adapted to express the B.t insecticidal toxin genes and variants in the plant cell by including in the vector a plant promoter. In addition to plant promoters, promoters from a variety of sources can be used efficiently in plant cells to express foreign genes. For example, one may use promoters of bacterial origin, such as the octopine synthase promoter, the nopaline synthase promoter, and the mannopine synthase promoter. Non-*Bacillus-thuringiensis* promoters can be used in some preferred embodiments. Promoters of plant virus origin may be used, for example, the $^{35}$S and 19S promoters of Cauliflower Mosaic Virus, a promoter from Cassava Vein Mosaic Virus, and the like. Plant promoters include, but are not limited to, ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, ubiquitin promoter, actin promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the leaves or seeds (e.g. zein, oleosin, napin, ACP (Acyl Carrier Protein) promoters), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO 2007/053482 A2), or phenoxy acids herbicides and aryloxyphenoxypropionates herbicides (see WO 2005107437 A2, A3). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein such as that of the subject invention, with one or more additional HT traits such as those mentioned above, plus one or more additional input traits (e.g. other insect resistance conferred by B.t.-derived or other insecticidal proteins, insect resistance conferred by mechanisms such as RNAi and the like, nematode resistance, disease resistance, stress tolerance, improved nitrogen utilization, and the like), or output traits (e.g. high oils content, healthy oil composition, nutritional improvement, and the like). Such combinations may be obtained either through conventional breeding (breeding stack) or jointly as a novel transformation event involving the simultaneous introduction of multiple genes (molecular stack). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

The transformed cells grow inside the plants in the usual manner. They can form germ cells and transmit the transformed trait(s) to progeny plants.

Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. In addition, methods for creating synthetic Bt genes for use in plants are known in the art (Stewart and Burgin, 2007). One non-limiting example of a preferred transformed plant is a fertile maize plant comprising a plant expressible gene encoding a Cry6Aa protein, and further comprising a second set of plant expressible genes encoding Cry3Aa proteins.

Transfer (or introgression) of the Cry6Aa- and Cry3Aa-determined trait(s) into inbred maize lines can be achieved by recurrent selection breeding, for example by backcrossing. In this case, a desired recurrent parent is first crossed to a donor inbred (the non-recurrent parent) that carries the appropriate gene(s) for the Cry-determined traits. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376).

Insect Resistance Management (IRM) Strategies.

Roush et al., for example, outlines two-toxin strategies, also called "pyramiding" or "stacking," for management of insecticidal transgenic crops. (The Royal Society. *Phil. Trans. R. Soc. Lond. B.* (1998) 353, 1777-1786).

On their website, the United States Environmental Protection Agency (epa.gov/oppbppd1/biopesticides/pips/bt_corn_refuge_2006.htm) publishes the following requirements for providing non-transgenic (i.e., non-B.t.) refuges (a block of non-Bt crops/corn) for use with transgenic crops producing a single Bt protein active against target pests.

"The specific structured requirements for corn borer-protected Bt (Cry1Ab or Cry1F) corn products are as follows:

Structured refuges:

20% non-Lepidopteran Bt corn refuge in Corn Belt;
50% non-Lepidopteran Bt refuge in Cotton Belt Blocks Internal (i.e., within the Bt field)
External (i.e., separate fields within ½ mile (¼ mile if possible) of the Bt field to maximize random mating)

In-field Strips

Strips must be at least 4 rows wide (preferably 6 rows) to reduce the effects of larval movement"

In addition, the National Corn Growers Association, on their website:

(ncga.com/insect-resistance-management-fact-sheet-bt-corn)

also provides similar guidance regarding the refuge requirements. For example:

"Requirements of the Corn Borer IRM:

Plant at least 20% of your corn acres to refuge hybrids
In cotton producing regions, refuge must be 50%
Must be planted within ½ mile of the refuge hybrids
Refuge can be planted as strips within the Bt field; the refuge strips must be at least 4 rows wide
Refuge may be treated with conventional pesticides only if economic thresholds are reached for target insect
Bt-based sprayable insecticides cannot be used on the refuge corn
Appropriate refuge must be planted on every farm with Bt corn"

As stated by Roush et al. (on pages 1780 and 1784 right column, for example), stacking or pyramiding of two different proteins each effective against the target pests and with little or no cross-resistance can allow for use of a smaller refuge. Roush suggests that for a successful stack, a refuge size of less than 10% refuge, can provide comparable resistance management to about 50% refuge for a single (non-pyramided) trait. For currently available pyramided Bt corn products, the U.S. Environmental Protection Agency requires significantly less (generally 5%) structured refuge of non-Bt corn be planted than for single trait products (generally 20%).

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

The above percentages, or similar refuge ratios, can be used for the subject double or triple stacks or pyramids.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted. All temperatures are in degrees Celsius.

Unless specifically indicated or implied, the terms "a", "an", and "the" signify "at least one" as used herein.

EXAMPLES

Example 1—Construction of Expression Plasmids Encoding Cry3Aa and Cry6Aa Full-Length Toxins Standard cloning methods were used in the construction of *Pseudomonas fluorescens* (Pf) expression plasmids engineered to produce full-length Cry3Aa and Cry6Aa Cry proteins, respectively. Restriction endonucleases from New England BioLabs (NEB; Ipswich, Mass.) were used for DNA digestion and T4 DNA Ligase from Invitrogen was used for DNA ligation. Plasmid preparations were performed using the Plasmid Mini kit (Qiagen, Valencia, Calif.), following the instructions of the supplier. DNA fragments were purified using the Millipore Ultrafree®-DA cartridge (Billerica, Mass.) after agarose Tris-acetate gel electrophoresis. The basic cloning strategy entailed subcloning the coding sequences (CDS) of full-length Cry proteins into pMYC1803 for Cry3Aa and into pDOW1169 for Cry6Aa at SpeI and XhoI (or SalI that is compatible with XhoI) restriction sites respectively, whereby they were placed under the expression control of the Ptac promoter and the rrnBT1T2 or rrnBT2 terminator from plasmid pKK223-3 (PL Pharmacia, Milwaukee, Wis.) respectively. pMYC1803 is a medium copy number plasmid with the RSF1010 origin of replication, a tetracycline resistance gene, and a ribosome binding site preceding the restriction enzyme recognition sites into which DNA fragments containing protein coding regions may be introduced (US Patent Application No. 20080193974). The expression plasmid for Cry3Aa (recombinant pMYC1803) was transformed by electroporation into a *P. fluorescens* strain MB214, recovered in SOC-Soy hydrolysate medium, and plated on Lysogeny broth (LB) medium containing 20 µg/ml tetracycline. The expression vector pDOW1169 is similar to pMYC1803 but pDOW1169 carries the pyrF gene encoding uracil, which was used as a marker for screening for transformants when a *P. fluorescens* uracil auxotrophic strain (such as DPf10) was used for transformation on a plate of M9 minimal medium that lacked of uracil (Schneider et al. 2005). Details of the microbiological manipulations are available from US Patent Application No. 20060008877, US Patent Application No. 20080193974, and US Patent Application No. 20080058262, incorporated herein by reference. Colonies were further screened by restriction digestion of miniprep plasmid DNA. Plasmid DNA of selected clones containing inserts was sequenced by contract with a commercial sequencing vendor such as eurofins MWG Operon (Huntsville, Ala.). Sequence data were assembled and analyzed using the Sequencher™ software (Gene Codes Corp., Ann Arbor, Mich.).

Example 2—Growth and Expression

Growth and expression analysis in shake-flask production of Cry3Aa and Cry6Aa toxins for characterization including Bt receptor binding and insect bioassay were accomplished by shake-flask-grown *P. fluorescens* strains harboring expression constructs (e.g. clone pMYC1334 for Cry3Aa and pDAB102018 for Cry6Aa). Seed culture for Cry3Aa grown in *P. fluorescens* medium overnight supplemented with 20 μg/ml tetracycline was used to inoculate 200 mL of the same medium with 20 μg/ml tetracycline. However, the seed culture for Cry6Aa was grown in M9 minimal broth overnight and was used to inoculate 200 mL of the *P. fluorescens* medium without antibiotic. Expressions of Cry3Aa and Cry6Aa toxins via the Ptac promoter were induced by addition of isopropyl-β-D-1-thiogalactopyranoside (IPTG) after an initial incubation of 24 hours at 28-30° C. with shaking at 300 rpm. Cultures were sampled at the time of induction and at various times post-induction. Cell density was measured by optical density at 600 nm ($OD_{600}$).

Example 3—Cell Fractionation and SDS-PAGE Analysis of Shake Flask Samples

At each sampling time, the cell density of the samples was adjusted to $OD_{600}$=20 and 1-mL aliquots were centrifuged at 14,000×g for five minutes. The cell pellets were frozen at −80° C. Soluble and insoluble fractions from frozen cell pellet samples were generated using EasyLyse™ Bacterial Protein Extraction Solution (EPICENTRE® Biotechnologies, Madison, Wis.). Each cell pellet was resuspended in 1 mL EasyLyse™ solution and further diluted 1:4 in lysis buffer and incubated with shaking at room temperature for 30 minutes. The lysate was centrifuged at 14,000 rpm for 20 minutes at 4° C. and the supernatant was recovered as the soluble fraction. The pellet (insoluble fraction) was then resuspended in an equal volume of phosphate buffered saline (PBS; 11.9 mM $Na_2HPO_4$, 137 mM NaCl, 2.7 mM KCl, pH7.4). Samples were mixed at 3:1 with 4× Laemmli sample buffer containing β-mercaptoethanol and boiled for 5 minutes prior to loading onto NuPAGE Novex 4-20% Bis-Tris gels (Invitrogen, Carlsbad, Calif.). Electrophoresis was performed in the recommended NuPAGE MOPS buffer. Gels were stained with the SimplyBlue™ Safe Stain according to the manufacturer's (Invitrogen) protocol and imaged using the Typhoon imaging system (GE Healthcare Life Sciences, Pittsburgh, Pa.).

Example 4—Inclusion Body Preparation

Cry protein inclusion body (IB) preparations were performed from *P. fluorescens* fermentations that produced insoluble B.t. insecticidal protein, as demonstrated by SDS-PAGE and MALDI-MS (Matrix Assisted Laser Desorption/Ionization Mass Spectrometry). *P. fluorescens* cell pellets created from 48 hours post induction were thawed in a 37° C. water bath. The cells were resuspended to 25% w/v in lysis buffer (50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (P8465 Sigma-Aldrich, St. Louis, Mo.) was added just prior to use only for Cry3Aa. The cells were suspended using a homogenizer at lowest setting (Tissue Tearor, BioSpec Products, Inc., Bartlesville, Okla.). Twenty five mg of lysozyme (Sigma L7651, from chicken egg white) was added to the cell suspension by mixing with a metal spatula, and the suspension was incubated at room temperature for one hour. The suspension was cooled on ice for 15 minutes, then sonicated using a Branson Sonifier 250 (two 1-minute sessions, at 50% duty cycle, 30% output). Cell lysis was checked by microscopy. An additional 25 mg of lysozyme was added if necessary, and the incubation and sonication were repeated. When cell lysis was confirmed via microscopy, the lysate was centrifuged at 11,500×g for 25 minutes (4° C.) to form the IB pellet, and the supernatant was discarded. The IB pellet was resuspended with 100 mL lysis buffer, homogenized with the hand-held mixer and centrifuged as above. The IB pellet was repeatedly washed by resuspension (in 50 mL lysis buffer), homogenization, sonication, and centrifugation until the supernatant became colorless and the IB pellet became firm and off-white in color. For the final wash, the IB pellet was resuspended in sterile-filtered (0.22 μm) distilled water containing 2 mM EDTA, and centrifuged. The final pellet was resuspended in sterile-filtered distilled water containing 2 mM EDTA, and stored in 1 mL aliquots at −80° C.

Example 5—SDS-PAGE Analysis and Quantification

SDS-PAGE analysis and quantification of protein in IB preparations were done by thawing a 1 mL aliquot of IB pellet and diluting 1:20 with sterile-filtered distilled water. The diluted sample was then boiled with 4× reducing sample buffer [250 mM Tris, pH6.8, 40% glycerol (v/v), 0.4% Bromophenol Blue (w/v), 8% SDS (w/v) and 8% β-Mercapto-ethanol (v/v)] and loaded onto a Novex® 4-20% Tris-Glycine, 12+2 well gel (Invitrogen) run with 1× Tris/Glycine/SDS buffer (Invitrogen). The gel was run for approximately 60 min at 200 volts then stained and destained by following the SimplyBlue™ Safe Stain (Invitrogen) procedures. Quantification of target bands was done by comparing densitometric values for the bands against Bovine Serum Albumin (BSA) samples run on the same gel to generate a standard curve using the Bio-Rad Quantity One software.

Example 6—Solubilization of Inclusion Bodies

Ten mL of inclusion body suspensions from *P. fluorescens* clones MR832 and DPf13032 (containing 50-70 mg/mL of Cry3Aa and Cry6Aa proteins respectively) were centrifuged at the highest setting of an Eppendorf model 5415C microfuge (approximately 14,000×g) to pellet the inclusions. The storage buffer supernatant was removed and replaced with 25 mL 50 mM CAPS [3-(cyclohexamino)1-propanesulfonic acid] buffer, pH10.5, for both Cry3Aa and Cry6Aa, in a 50 mL conical tube respectively. Inclusions were resuspended using a pipette and vortexed to mix thoroughly. The tubes were placed on a gently rocking platform at 4° C. overnight to extract full-length Cry3Aa and Cry6Aa proteins. The extracts were centrifuged at 30,000×g for 30 min at 4° C., and saved the resulting supernatants containing solubilized full-length Cry proteins.

Example 7—Truncation of Full-Length Protoxin

Full-length Cry3Aa was digested with trypsin to generate an active form of the Cry protein resistant to further trypsin digestion. Specifically, the solubilized full-length Cry3Aa was incubated with trypsin (bovine pancreas) (Sigma, St. MO) at (20:1=Cry protein:enzyme, w/w) in the 100 mM sodium carbonate buffer, pH11, at room temperature for 1-3 hours. Complete activation or truncation was confirmed by SDS-PAGE analysis. The molecular mass of the full-length Cry3Aa was ≈73 kDa, and the trypsin core was ≈55 kDa, respectively. The amino acid sequences of the full-length and trypsin core of Cry3Aa are provided as SEQ ID 1 and SEQ ID 2. The full-length Cry6Aa is significantly more active to target insect corn rootworm than its either chymotrypsin or trypsin core. Thus, the full-length Cry6Aa was used for binding assays. The amino acid sequence of the full-length Cry6Aa is provided as SEQ ID 3.

Example 8—Purification of Cry Toxins

The trypsinized Cry3Aa and full-length Cry6Aa were further purified using an ion-exchange chromatography system. Specifically, they were further purified using ATKA Explorer liquid chromatography system (Amersham Biosciences). For both Cry3Aa and Cry6Aa, buffer A was 10 mM CAPS buffer, pH 10.5, and buffer B was 10 mM CAPS buffer, pH 10.5+1 M NaCl. A Capto Q (5 ml) column (GE) was used. After the column was fully equilibrated using the buffer A, a Cry toxin solution was injected into the column at a flow rate of 5 ml/min. Elution was performed using gradient 0-100% of the buffer B at 5 ml/min with 1 ml/fraction. After SDS-PAGE analysis of the selected fractions to further select fractions containing the best quality target protein, pooled those fractions. The buffer was changed for the both purified Cry3Aa trypsin core and full-length Cry6Aa to 10 mM CAPS, pH 10.5 through dialysis. The samples were saved at 4° C. for later binding assay after being quantified using SDS-PAGE and the Typhoon imaging system (GE) analyses with BSA as a standard.

Example 9—BBMV Preparations

Brush border membrane vesicle (BBMV) preparations of insect midguts have been widely used for Cry toxin receptor binding assays. The BBMV preparations used in this invention were prepared from isolated midguts of third instars of the western corn rootworm (*Diabrotica virgifera virgifera* LeConte) using the method described by Wolfersberger et al. (1987). Leucine aminopeptidase was used as a marker of membrane proteins in the preparation and Leucine aminopeptidase activities of crude homogenate and BBMV preparation were determined as previously described (Li et al. 2004a). Protein concentration of the BBMV preparation was measured using the Bradford method (1976).

Example 10—125I Labeling

Purified Cry3Aa trypsin core and full-length Cry6Aa were labeled using $^{125}$I for saturation and competition binding assays. To ensure the radio-labeling does not abolish the biological activity of the Cry toxins, cold iodination was conducted using NaI by following the instructions of Pierce® Iodination Beads (Pierce Biotechnology, Thermo Scientific, Rockford Ill.). Bioassay results indicated that both iodinated Cry3Aa trypsin core and full-length Cry6Aa remained active against the larvae of the western corn rootworm. $^{125}$I-Cry3Aa and $^{125}$I-Cry6Aa were obtained with Pierce® Iodination Beads (Pierce) and Na$^{125}$I. Zeba™ Desalt Spin Columns (Pierce) were used to remove unincorporated or free Na$^{125}$I from the iodinated protein. The specific radio-activities of the iodinated Cry proteins ranged from 1-5 uCi/ug. Multiple replicates of labeling and binding assays were conducted.

Example 11—Saturation Binding Assays

Figure 1:
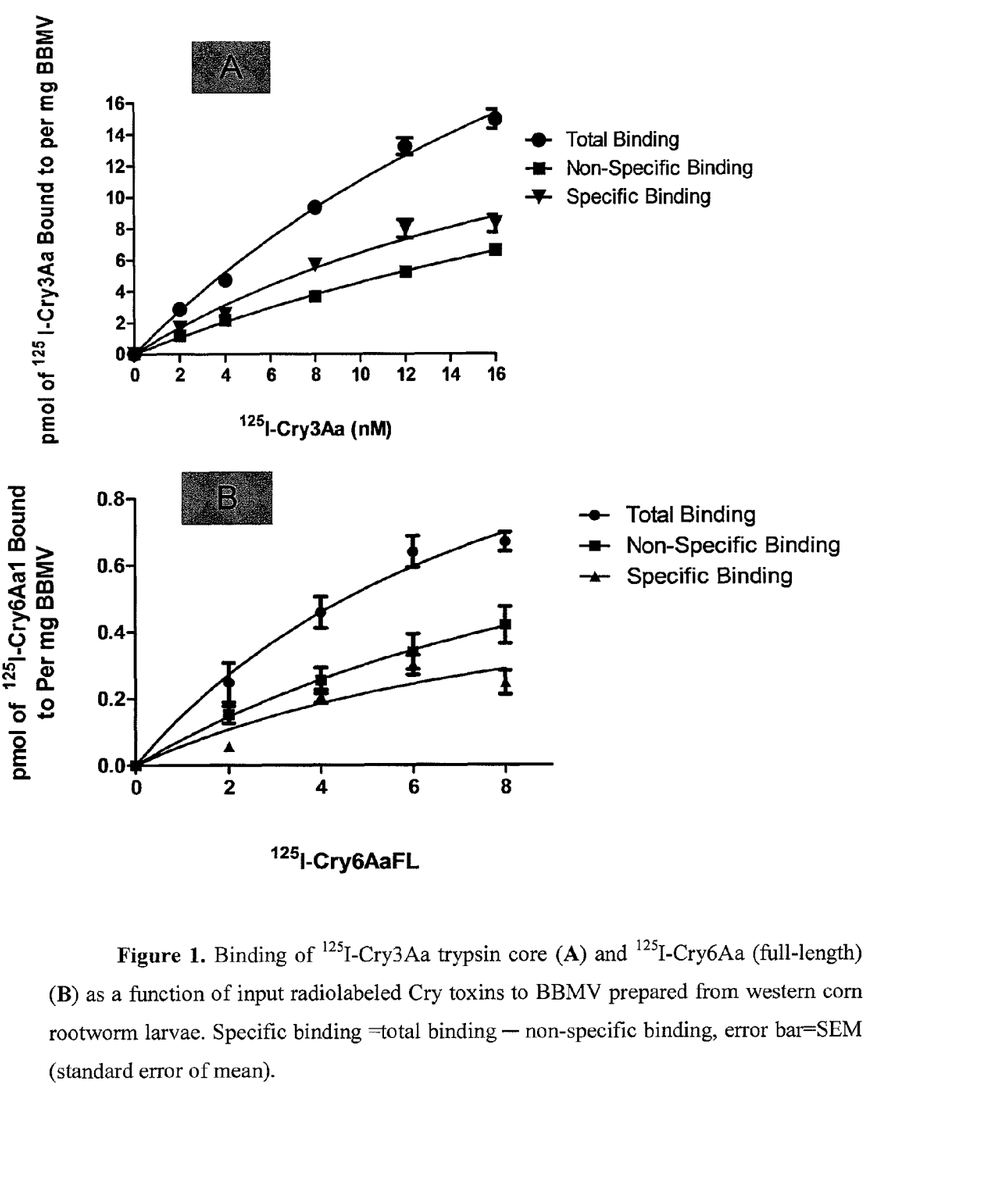
FIG. 1. Binding of $^{125}$I-Cry3Aa trypsin core (FIG. 1A) and $^{125}$I-Cry6Aa1 (full-length) (FIG. 1B) as a function of input radiolabeled Cry toxins to BBMV prepared from western corn rootworm larvae. Specific binding=total binding−non-specific binding, error bar=SEM (standard error of mean).

Saturation binding assays were performed using $^{125}$I-labeled Cry toxins as described previously (Li et al. 2004b). To determine specific binding and estimate the binding affinity (disassociation constant, Kd) and binding site concentration (the maximum amount of toxin specifically bound to a given amount of BBMV, Bmax) of Cry3Aa and Cry6Aa to the insect BBMV, a series of increasing concentrations of either $^{125}$I-Cry3Aa or $^{125}$I-Cry6Aa were incubated with a given concentration (0.1 mg/ml) of the insect BBMV respectively, in 150 ul of 20 mM Bis-Tris, pH 6.0, 150 mM KCl, supplemented with 0.1% BSA at room temperature for 60 min with gentle shaking Toxin bound to BBMV was separated from free toxins in the suspension by centrifugation at 20,000×g at room temperature for 8 min. The pellet was washed twice with 900 ul of ice-cold the same buffer containing 0.1% BSA. The radio-activity remaining in the pellet was measured with a COBRAII Auto-Gamma counter (Packard, a Can berra company) and considered total binding. Another series of binding reactions were setup at side by side, and a 500-1,000-fold excess of unlabeled corresponding toxin was included in each of the binding reactions to fully occupy all specific binding sites on the BBMV, which was used to determine non-specific binding. Specific binding was estimated by subtracting the non-specific binding from the total binding. The Kd and Bmax values of these toxins were estimated using the toxin molecule number (pmole) specifically bound to per microgram BBMV protein against the concentrations of the labeled toxin used by running GraphPad Prism 5.01 (GraphPad Software, San Diego, Calif.). The charts were made using either Microsoft Excel or GraphPad Prism program. The experiments were replicated at least three times. These binding experiments demonstrated that both $^{125}$I-Cry3Aa and $^{125}$I-Cry6Aa were able to specifically bind to the BBMV (FIGS. 1A and 1B). $^{125}$I-Cry3Aa and $^{125}$I-Cry6Aa had a binding affinity Kd=24.0±9.76, 10.14±8.29 (nM), and a binding site concentration Bmax=21.97±5.99 pmole/mg, 0.66±0.33 (pmole/mg BBMV), respectively.

Example 12—Competition Binding Assays

Figure 2:
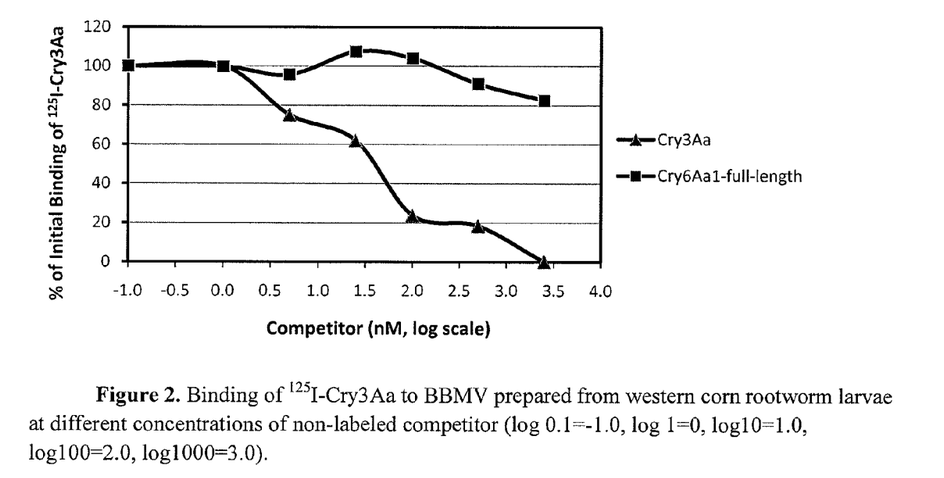
FIG. 2. Binding of $^{125}$I-Cry3Aa to BBMV prepared from western corn rootworm larvae at different concentrations of non-labeled competitor (log 0.1=−1.0, log 1=0, log 10=1.0, log 100=2.0, log 1000=3.0).

Competition binding assays were further conducted to determine if Cry3Aa trypsin core and full-length Cry6Aa share BBMV binding sites. For Cry3Aa homologous competition binding assays, increasing amounts (0-2500 nM) of unlabeled Cry3Aa were first mixed with 5 nM labeled Cry3Aa, and then incubated with a given concentration (0.1 mg/ml) of BBMV at room temperature for 60 min, respectively. The percentages of bound $^{125}$I-Cry3Aa with BBMV were determined for each of the reactions as compared to the initial specific binding at absence of unlabeled competitor. Heterologous competition binding assay between $^{125}$I-Cry3Aa and unlabeled Cry6Aa was performed to identify if they share a same set of receptor(s). This was achieved by increasing the amount of unlabeled Cry6Aa as a competitor included in the reactions to compete for the putative receptor(s) on the BBMV with the labeled Cry3Aa. The experiment was replicated at least three times. The experimental results demonstrated that Cry3Aa was able to displace itself about 60% when the molar concentration increased to approximately 2500 nM (500 folds excess compared to 5 nM $^{125}$I-Cry3Aa). The remaining about 40% was considered nonspecific binding that was not able to be displaced based on the saturation binding result described elsewhere and the definition of non-specific binding, and thus the non-specific binding was subtracted and not shown here. This suggests that the specific binding was completely displaced by 500-fold excess unlabeled Cry3Aa (FIG. 2). However, Cry6Aa was not able to displace $^{125}$I-Cry3Aa. These data indicate that Cry3Aa does not share a receptor or a binding site with Cry6Aa.

REFERENCES

Bradford, M. M. 1976. A rapid and sensitive method for the quantitation of microgram quantities of protein utilizing the principle of protein-dye binding, Anal. Biochem. 72, 248-254.

Li, H., Oppert, B., Higgins, R. A., Huang, F., Zhu, K. Y., Buschman, L. L., 2004a. Comparative analysis of proteinase activities of *Bacillus thuringiensis*-resistant and -susceptible *Ostrinia nubilalis* (Lepidoptera: Crambidae). Insect Biochem. Mol. Biol. 34, 753-762.

Li, H., Oppert, B., Gonzalez-Cabrera, J., Ferré, J., Higgins, R. A., Buschman, L. L. and Zhu, K. Y. and Huang, F. 2004b. Binding analysis of Cry1Ab and Cry1Ac with membrane vesicles from *Bacillus thuringiensis*-resistant and -susceptible *Ostrinia nubilalis* (Lepidoptera: Crambidae). *Biochem. Biophys. Res. Commun.* 323, 52-57.

Schneider, J. C. Jenings A F, Mun D M, McGovern P M, Chew L C. 2005. Auxotrophic markers pyrF and proC can replace antibiotic markers on protein production plasmids in high-cell-density *Pseudomonas fluorescens* fermentation. Biotechnology Progress 21, 343-348.

Wolfersberger, M. G., Luthy, P., Maurer, A., Parenti, P., Sacchi, F., Giordana, B., Hanozet, G. M., 1987. Preparation and partial characterization of amino acid transporting brush border membrane vesicles from the larval midgut of the cabbage butterfly (*Pieris brassicae*). Comp. Biochem. Physiol. 86A, 301-308.

US Patent Application No. 20080193974. 2008. BACTERIAL LEADER SEQUENCES FOR INCREASED EXPRESSION US Patent Application No. 20060008877, 2006. Expression systems with sec-system secretion.

US Patent Application No. 20080058262, 2008. rPA optimization.

We claim:

1. A transgenic corn plant that produces a Cry3Aa insecticidal protein and a Cry6Aa insecticidal protein, wherein said Cry3Aa protein consists of SEQ ID NO:2, and said Cry6Aa protein is full-length and consists of SEQ ID NO:3, wherein the combination of the Cry3Aa insecticidal protein and the Cry6Aa insecticidal protein is insecticidally effective against corn rootworm, and wherein the Cry3Aa insecticidal protein and the Cry6Aa insecticidal protein do not share a receptor binding site in corn rootworm gut.

2. The transgenic plant of claim 1, wherein said plant further produces a third insecticidal protein selected from the group consisting of Cry3Ba, Cry34Ab, and Cry35Ab.

3. A seed of the transgenic plant according to claim 1, wherein said seed comprises DNA encoding said proteins.

4. A plurality of plants comprising a plurality of transgenic plants according to claim 1.

5. The plurality of plants of claim 4, said plurality of plants further comprising non-Bt refuge plants, wherein said refuge plants comprise less than 40% of all crop plants in said plurality of plants.

6. The plurality of plants of claim 5, wherein said refuge plants comprise less than 30% of all crop plants in said plurality of plants.

7. The plurality of plants of claim 5, wherein said refuge plants comprise less than 20% of all crop plants in said plurality of plants.

8. The plurality of plants of claim 5, wherein said refuge plants comprise less than 10% of all crop plants in said plurality of plants.

9. The plurality of plants of claim 5, wherein said refuge plants comprise less than 5% of all crop plants in said plurality of plants.

10. The plurality of plants of claim 4, wherein said plurality of plants lacks refuge plants.

11. The plurality of plants of claim 5, wherein said refuge plants are in blocks or strips.

12. A mixture of seeds comprising refuge seeds from non-Bt refuge plants, and a plurality of seeds of claim 3, wherein said refuge seeds comprise less than 40% of all the seeds in the mixture.

13. The mixture of seeds of claim 12, wherein said refuge seeds comprise less than 30% of all the seeds in the mixture.

14. The mixture of seeds of claim 12, wherein said refuge seeds comprise less than 20% of all the seeds in the mixture.

15. The mixture of seeds of claim 12, wherein said refuge seeds comprise less than 10% of all the seeds in the mixture.

16. The mixture of seeds of claim 12, wherein said refuge seeds comprise less than 5% of all the seeds in the mixture.

17. A method of delaying or preventing the development of resistance to a Cry protein by a corn rootworm insect, said method comprising planting seeds to produce the plurality of plants of claim 4, wherein the plurality of plants expresses the Cry3Aa insecticidal protein and the Cry6Aa insecticidal protein.

18. The plurality of plants of claim 4, wherein said plants occupy more than 10 acres.

19. A plant cell of the plant of claim 1, wherein said plant cell produces said Cry3Aa insecticidal protein and said Cry6Aa insecticidal protein.

20. A method of producing the plant cell of claim 19, said method comprising transforming the plant with a DNA encoding said Cry3Aa insecticidal protein and a DNA encoding said Cry6Aa insecticidal protein.

21. A method of controlling a corn rootworm insect, said method comprising contacting said insect with the transgenic plant of claim 1, wherein the plant expresses an insecticidally effective amount of said Cry3Aa insecticidal protein and said Cry6Aa insecticidal protein.

* * * * *

SEQUENCE LISTING

```
<160> NUMBER OF SEQ ID NOS: 3

<210> SEQ ID NO 1
<211> LENGTH: 644
<212> TYPE: PRT
<213> ORGANISM: Bacillus thuringiensis

<400> SEQUENCE: 1

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125
```

```
Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540
```

-continued

```
Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 2
<211> LENGTH: 486
<212> TYPE: PRT
<213> ORGANISM: Bacillus thuringiensis

<400> SEQUENCE: 2

Asn Pro His Ser Gln Gly Arg Ile Arg Glu Leu Phe Ser Gln Ala Glu
1               5                   10                  15

Ser His Phe Arg Asn Ser Met Pro Ser Phe Ala Ile Ser Gly Tyr Glu
            20                  25                  30

Val Leu Phe Leu Thr Thr Tyr Ala Gln Ala Ala Asn Thr His Leu Phe
        35                  40                  45

Leu Leu Lys Asp Ala Gln Ile Tyr Gly Glu Glu Trp Gly Tyr Glu Lys
    50                  55                  60

Glu Asp Ile Ala Glu Phe Tyr Lys Arg Gln Leu Lys Leu Thr Gln Glu
65                  70                  75                  80

Tyr Thr Asp His Cys Val Lys Trp Tyr Asn Val Gly Leu Asp Lys Leu
                85                  90                  95

Arg Gly Ser Ser Tyr Glu Ser Trp Val Asn Phe Asn Arg Tyr Arg Arg
            100                 105                 110

Glu Met Thr Leu Thr Val Leu Asp Leu Ile Ala Leu Phe Pro Leu Tyr
        115                 120                 125

Asp Val Arg Leu Tyr Pro Lys Glu Val Lys Thr Glu Leu Thr Arg Asp
    130                 135                 140

Val Leu Thr Asp Pro Ile Val Gly Val Asn Asn Leu Arg Gly Tyr Gly
145                 150                 155                 160

Thr Thr Phe Ser Asn Ile Glu Asn Tyr Ile Arg Lys Pro His Leu Phe
                165                 170                 175

Asp Tyr Leu His Arg Ile Gln Phe His Thr Arg Phe Gln Pro Gly Tyr
            180                 185                 190

Tyr Gly Asn Asp Ser Phe Asn Tyr Trp Ser Gly Asn Tyr Val Ser Thr
        195                 200                 205

Arg Pro Ser Ile Gly Ser Asn Asp Ile Ile Thr Ser Pro Phe Tyr Gly
    210                 215                 220

Asn Lys Ser Ser Glu Pro Val Gln Asn Leu Glu Phe Asn Gly Glu Lys
225                 230                 235                 240

Val Tyr Arg Ala Val Ala Asn Thr Asn Leu Ala Val Trp Pro Ser Ala
                245                 250                 255

Val Tyr Ser Gly Val Thr Lys Val Glu Phe Ser Gln Tyr Asn Asp Gln
            260                 265                 270
```

```
Thr Asp Glu Ala Ser Thr Gln Thr Tyr Asp Ser Lys Arg Asn Val Gly
            275                 280                 285

Ala Val Ser Trp Asp Ser Ile Asp Gln Leu Pro Pro Glu Thr Thr Asp
    290                 295                 300

Glu Pro Leu Glu Lys Gly Tyr Ser His Gln Leu Asn Tyr Val Met Cys
305                 310                 315                 320

Phe Leu Met Gln Gly Ser Arg Gly Thr Ile Pro Val Leu Thr Trp Thr
                325                 330                 335

His Lys Ser Val Asp Phe Phe Asn Met Ile Asp Ser Lys Lys Ile Thr
            340                 345                 350

Gln Leu Pro Leu Val Lys Ala Tyr Lys Leu Gln Ser Gly Ala Ser Val
        355                 360                 365

Val Ala Gly Pro Arg Phe Thr Gly Gly Asp Ile Ile Gln Cys Thr Glu
    370                 375                 380

Asn Gly Ser Ala Ala Thr Ile Tyr Val Thr Pro Asp Val Ser Tyr Ser
385                 390                 395                 400

Gln Lys Tyr Arg Ala Arg Ile His Tyr Ala Ser Thr Ser Gln Ile Thr
                405                 410                 415

Phe Thr Leu Ser Leu Asp Gly Ala Pro Phe Asn Gln Tyr Tyr Phe Asp
            420                 425                 430

Lys Thr Ile Asn Lys Gly Asp Thr Leu Thr Tyr Asn Ser Phe Asn Leu
        435                 440                 445

Ala Ser Phe Ser Thr Pro Phe Glu Leu Ser Gly Asn Asn Leu Gln Ile
    450                 455                 460

Gly Val Thr Gly Leu Ser Ala Gly Asp Lys Val Tyr Ile Asp Lys Ile
465                 470                 475                 480

Glu Phe Ile Pro Val Asn
                485

<210> SEQ ID NO 3
<211> LENGTH: 475
<212> TYPE: PRT
<213> ORGANISM: Bacillus thuringiensis

<400> SEQUENCE: 3

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160
```

-continued

```
Arg Cys Gly Ile Leu Ile Lys Glu Ala Lys Gln Tyr Glu Glu Ala Ala
                165             170             175

Lys Asn Ile Val Thr Ser Leu Asp Gln Phe Leu His Gly Asp Gln Lys
            180             185             190

Lys Leu Glu Gly Val Ile Asn Ile Gln Lys Arg Leu Lys Glu Val Gln
        195             200             205

Thr Ala Leu Asn Gln Ala His Gly Glu Ser Ser Pro Ala His Lys Glu
    210             215             220

Leu Leu Glu Lys Val Lys Asn Leu Lys Thr Thr Leu Glu Arg Thr Ile
225             230             235             240

Lys Ala Glu Gln Asp Leu Glu Lys Lys Val Glu Tyr Ser Phe Leu Leu
            245             250             255

Gly Pro Leu Leu Gly Phe Val Val Tyr Glu Ile Leu Glu Asn Thr Ala
            260             265             270

Val Gln His Ile Lys Asn Gln Ile Asp Glu Ile Lys Lys Gln Leu Asp
        275             280             285

Ser Ala Gln His Asp Leu Asp Arg Asp Val Lys Ile Ile Gly Met Leu
    290             295             300

Asn Ser Ile Asn Thr Asp Ile Asp Asn Leu Tyr Ser Gln Gly Gln Glu
305             310             315             320

Ala Ile Lys Val Phe Gln Lys Leu Gln Gly Ile Trp Ala Thr Ile Gly
            325             330             335

Ala Gln Ile Glu Asn Leu Arg Thr Thr Ser Leu Gln Glu Val Gln Asp
            340             345             350

Ser Asp Asp Ala Asp Glu Ile Gln Ile Glu Leu Glu Asp Ala Ser Asp
            355             360             365

Ala Trp Leu Val Val Ala Gln Glu Ala Arg Asp Phe Thr Leu Asn Ala
    370             375             380

Tyr Ser Thr Asn Ser Arg Gln Asn Leu Pro Ile Asn Val Ile Ser Asp
385             390             395             400

Ser Cys Asn Cys Ser Thr Thr Asn Met Thr Ser Asn Gln Tyr Ser Asn
            405             410             415

Pro Thr Thr Asn Met Thr Ser Asn Gln Tyr Met Ile Ser His Glu Tyr
            420             425             430

Thr Ser Leu Pro Asn Asn Phe Met Leu Ser Arg Asn Ser Asn Leu Glu
            435             440             445

Tyr Lys Cys Pro Glu Asn Asn Phe Met Ile Tyr Trp Tyr Asn Asn Ser
    450             455             460

Asp Trp Tyr Asn Asn Ser Asp Trp Tyr Asn Asn
465             470             475
```